(12) United States Patent
Pearl, Jr. et al.

(10) Patent No.: US 10,072,979 B2
(45) Date of Patent: Sep. 11, 2018

(54) INTEGRATED COMPUTATIONAL ELEMENTS CONTAINING A QUANTUM DOT ARRAY AND METHODS FOR USE THEREOF

(71) Applicant: Halliburton Energy Services, Inc., Houston, TX (US)

(72) Inventors: William Cecil Pearl, Jr., Spring, TX (US); David L. Perkins, The Woodlands, TX (US); Megan Renee Pearl, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 65 days.

(21) Appl. No.: 15/324,116

(22) PCT Filed: Apr. 26, 2016

(86) PCT No.: PCT/US2016/029291
§ 371 (c)(1),
(2) Date: Jan. 5, 2017

(87) PCT Pub. No.: WO2017/188930
PCT Pub. Date: Nov. 2, 2017

(65) Prior Publication Data
US 2018/0180475 A1    Jun. 28, 2018

(51) Int. Cl.
*G01N 21/25* (2006.01)
*G01J 3/02* (2006.01)
(Continued)

(52) U.S. Cl.
CPC ............... *G01J 3/0205* (2013.01); *G01J 3/30* (2013.01); *G06E 1/045* (2013.01); *E21B 49/08* (2013.01)

(58) Field of Classification Search
CPC ........ G01J 3/02; G01J 3/51; G01J 3/30; G01J 3/26; G01J 9/00; G06E 1/045;
(Continued)

(56) References Cited

U.S. PATENT DOCUMENTS

| 7,895,880 B2 | 3/2011 | Fritz et al. |
| 9,151,668 B1 | 10/2015 | Nagarkar et al. |

(Continued)

FOREIGN PATENT DOCUMENTS

| WO | 2015134036 A1 | 9/2015 |

OTHER PUBLICATIONS

Nagy et al., Comprehensive Analysis of the Effects of CdSe Quantum Dot Size, Surface Charge, and Functionalization on Primary Human Lung Cells, ACS Nano Article, vol. 6, No. 6, pp. 4748-4762, 2012.
(Continued)

*Primary Examiner* — Abdullahi Nur
(74) *Attorney, Agent, or Firm* — McDermott Will & Emery LLP

(57) ABSTRACT

Integrated computational elements having alternating layers of materials may be problematic to configure toward mimicking some regression vectors. Further, they sometimes may be inconvenient to use within highly confined locales. Integrated computational elements containing a quantum dot array may address these issues. Optical analysis tools with an integrated computational element can comprise: an electromagnetic radiation source that provides electromagnetic radiation to an optical pathway; an integrated computational element positioned within the optical pathway, the integrated computational element comprising a quantum dot array having a plurality of quantum dots disposed at a plurality of set array positions; and a detector that receives the electromagnetic radiation from the optical pathway after the electromagnetic radiation has optically interacted with a sample and the integrated computational element. Optical
(Continued)

interaction of electromagnetic radiation with the quantum dots at one or more set array positions can substantially mimic a regression vector for a sample characteristic.

24 Claims, 4 Drawing Sheets

(51) Int. Cl.
    *G06E 1/04*         (2006.01)
    *G01J 3/30*         (2006.01)
    *E21B 49/08*       (2006.01)

(58) Field of Classification Search
    CPC .... G01N 21/255; G01N 21/17; G01N 21/314; G01N 2021/31
    See application file for complete search history.

(56) References Cited

U.S. PATENT DOCUMENTS

2013/0284894 A1   10/2013   Freese et al.
2013/0284896 A1*  10/2013   Freese ................... G01N 21/17
                                                          250/208.2
2016/0018339 A1    1/2016   Perkins

OTHER PUBLICATIONS

Chen, O. et al., Synthesis of Metal-Selenide Nanocrystals Using Selenium Dioxide as the Selenium Precursor, Angew. Chem. Int. Ed. 47, 8638-8641 (2008).

Qu, L. et al., Alternative Routes Toward High Quality CdSe Nanocrystals, Nano Lett. 1, 333-337 (2001).

Peng et al., Formation of High-Quality CdTe, CdSe, and CdS Nanocrystals Using CdO as Precursor, J. Am Chem. Soc. 123, 183-184 (2001).

Cao et al., One-Pot Synthesis of High-Quality Zinc-Blend CdS Nanocrystals, J. Am. Chem. Soc 126, 14336-14337 (2004).

McDonald et al., Solution-Processed PbS Quantum Dot Infrared Photodetectors and Photovoltaics, Nature Materials, vol. 4, pp. 138-142, 2005.

Pietryga et al., Pushing the Band Gap Envelope: Mid-Infrared Emitting Colloidal PbSe Quantum Dots, J. Am. Chem. Soc., 2004, 126, 11752-11753.

Chen et al., "Giant" Multishell CdSe Nanocrystal Quantum Dots with Suppressed Blinking, J. Am. Chem. Soc. 2008, 130, 5026-5027.

Kim, Type-II Quantum Dots: CdTe/CdSe(Core/Shell) and CdSe/ZnTe(Core/Shell) Heterostructures, J. Am. Chem. Soc. 2003, 125, 11466-11467.

Plass et al., Quantum Dot Sensitization of Organic-Inorganic Hybrid Solar Cells, J. Phys. Chem. B 2002, 106, 7578-7580.

Bao et al., "A colloidal quantum dot spectrometer," Nature 2015.

Kongkanand et al., "Quantum Dot Solar Cells. Tuning Photoresponse through Size and Shape Control of CdSe-TiO2 Architecture," JACS Articles, Mar. 1, 2008.

Jin et al., "Control of the Optical Properties of Quantum Dots by Surface Coating with Calix[n]arene Carboxylic Acids," JACS Article Jul. 4, 2006.

ISR/WO for PCT/US2016/029291 dated Dec. 15, 2016.

* cited by examiner

INTEGRATED COMPUTATIONAL ELEMENTS CONTAINING A QUANTUM DOT ARRAY AND METHODS FOR USE THEREOF

BACKGROUND

The present disclosure generally relates to optical analysis tools and, more specifically, to optical analysis tools having an integrated computational element that can be reconfigured for analyzing a characteristic of a sample.

Spectroscopic analyses are well known for their versatility for detecting a wide variety of substances by obtaining and analyzing a spectrum. Most spectroscopic instruments are general purpose and are not configured to detect any one particular substance or class of substance. Accordingly, involved and time-consuming spectral processing and/or sample preparation operations may be needed to analyze for a particular substance within a given sample to obtain a satisfactory spectrum, especially when multiple detectable substances are present. Although spectroscopic analyses can often be routinely carried out under regulated laboratory conditions, they can be considerably more difficult to transition into less controlled environments, such as the oilfield and other process settings, where operational conditions may damage and/or limit the accuracy of conventional spectroscopic equipment and techniques.

Optical computing devices represent a distinct alternative to conventional spectroscopic equipment and techniques. As used herein, the term "optical computing device" will refer to an optical analysis tool configured to receive an input of electromagnetic radiation from a sample and produce an output of electromagnetic radiation from a processing element that is diagnostic of a characteristic of the sample. Optical computing devices utilize an integrated computational element (ICE), also referred to as an "ICE core," which is a processing element that is specifically designed to analyze for a given component or characteristic of interest in a sample upon optical interaction of electromagnetic radiation therewith. In analyzing for the characteristic, a spectrum is not produced by the optical computing device. Instead, the integrated computational element determines a dot product for the regression vector of the characteristic, as discussed in further detail below.

As used herein, the term "characteristic" will refer to a substance's concentration in a sample or a derived physical property for the sample. The transmission or reflection function of an integrated computational element may represent the regression vector for a characteristic of interest, and the transmission or reflection function may be weighted with respect to wavelength by taking the dot product of the regression vector over the wavelength space being analyzed. Accordingly, upon optically interacting electromagnetic radiation with a sample and with an integrated computational element, the electromagnetic radiation may change in a known and specific way that may be representative of the characteristic's magnitude in the sample. Following receipt of the electromagnetic radiation at a detector and calculation of the dot product, a numerical output from the detector can be correlated to the characteristic of interest. Even though a complex mixture of substances may be present in a given sample, an integrated computational element may be able to distinguish and analyze for a particular substance or characteristic based upon the unique regression vector represented by the integrated computational element.

Optical computing devices may be advantageous compared to conventional spectroscopic techniques, since analyses may be conducted rapidly, often in real-time, with limited to no sample preparation involved. Rather than obtaining an optical spectrum as in conventional spectroscopic techniques, which may require further interpretation and deconvolution to take place for analyzing a characteristic, the numerical output produced by optical computing devices may be directly correlated to a characteristic of interest. Optical computing devices are also much more rugged than conventional spectroscopic equipment and can be deployed in locales where spectroscopic analyses may otherwise be problematic. Accordingly, optical computing devices may often be desirable for analyzing complex mixtures in various process environments, such as those encountered in the oilfield industry.

Optical computing analyses may utilize a single integrated computational element or, more commonly, a plurality of integrated computational elements. A plurality of integrated computational elements may be used to analyze for multiple characteristics of a sample or a single sample characteristic. Using multiple integrated computational elements to analyze for a single sample characteristic may involve optically interacting electromagnetic radiation with the sample and with multiple integrated computational elements in sequence or by computationally combining the numerical outputs of two or more integrated computational elements with one another. Benefits that may be realized when utilizing multiple integrated computational elements in the analysis of a single characteristic of interest include, but are not limited to, increased analytical sensitivity, signal normalization and combinations thereof.

Conventionally, integrated computational elements refer to optical processing elements containing a plurality of optical thin film layers formed from various materials whose indices of refraction and thicknesses may vary between each layer. Oftentimes, conventional integrated computational elements may contain a plurality of alternating layers of materials having high and low indices of refraction such that the layer compositions, thicknesses, and ordering may be chosen, based upon calculations, to selectively transmit or reflect predetermined fractions of electromagnetic radiation at different wavelengths. In doing so, the integrated computational element essentially may function as an interference filter, and the integrated computational element may substantially mimic the regression vector corresponding to a particular characteristic of interest in a sample. Taking the dot product of the regression vector allows the characteristic to be determined.

Although conventional integrated computational elements may have exceptional utility in a variety of analyses, they are not without their limitations. Although design calculations and thin-layer deposition techniques for producing conventional integrated computational elements are well understood, they can be time-consuming and expensive to carry out, and there is no guarantee that a given integrated computational element will sufficiently mimic a regression vector as intended upon testing and/or deployment. Since the regression vectors for various sample characteristics generally differ, multiple integrated computational elements may need to be designed and tested for analyzing multiple characteristics. Furthermore, when the regression vector for a given sample characteristic is complex, the calculations and layer deposition pattern for the integrated computational element may be correspondingly complex. Finally, conventional integrated computational elements often function most effectively in mimicking a sample characteristic's regression vector in the near-infrared region of the electromagnetic spectrum, and it can often be difficult to modify the design of the integrated computational element to extend the working wavelength range into other spectral regions, such as the mid- and far-infrared and ultraviolet regions.

Another potential limitation associated with conventional integrated computational elements involves the deployment of multiple integrated computational elements in an optical analysis tool. Multiple integrated computational elements may be disposed along an extended optical pathway or upon a movable assembly that allows different integrated computational elements to be exposed to electromagnetic radiation in the optical pathway at various points in time (e.g., through lateral or rotational motion of the movable assembly). Either configuration, however, can result in a profile that is too bulky to fit effectively within confined operating locales. Extreme operating environments can also be taxing toward mechanical operating mechanisms used to produce lateral or rotational motion in such instances, not to mention possible footprint and reliability issues associated with the mechanical operating mechanism itself. Furthermore, it can be problematic in some deployment locales, such as within a subterranean wellbore, to supply sustained operating power for producing ongoing lateral or rotational motion.

BRIEF DESCRIPTION OF THE DRAWINGS

The following figures are included to illustrate certain aspects of the present disclosure and should not be viewed as exclusive embodiments. The subject matter disclosed is capable of considerable modifications, alterations, combinations, and equivalents in form and function, as will occur to one having ordinary skill in the art and the benefit of this disclosure.

DETAILED DESCRIPTION

The present disclosure generally relates to optical analysis tools and, more specifically, to optical analysis tools having an integrated computational element that can be reconfigured for analyzing a characteristic of a sample.

One or more illustrative embodiments incorporating the features of the present disclosure are presented herein. Not all features of a physical implementation are necessarily described or shown in this application for the sake of clarity. It is to be understood that in the development of a physical implementation incorporating the embodiments of the present disclosure, numerous implementation-specific decisions may be made to achieve the developer's goals, such as compliance with system-related, business-related, government-related and other constraints, which may vary by implementation and from time to time. While a developer's efforts might be time-consuming, such efforts would be, nevertheless, a routine undertaking for one having ordinary skill in the art and the benefit of this disclosure.

As discussed above, optical analysis tools containing an integrated computational element may provide a number of advantages over conventional spectroscopic techniques, not to mention wet chemical analyses. In this regard, integrated computational elements may be specifically designed to analyze for a particular characteristic of interest, even in samples containing a complex mixture of substances. A plurality of integrated computational elements may be used to conduct analyses for a single characteristic or for multiple characteristics. However, optical analysis tools containing conventional integrated computational elements can sometimes be limited in terms of operational performance, design and fabrication complexity, and operational footprint. Further, once one or more integrated computational elements have been fabricated and deployed for analyzing a sample, there are only limited ways that their output data can be computationally manipulated to determine a characteristic. In the event that a given integrated computational element does not perform as intended when deployed, there may be little choice but to remove the optical analysis tool from its operating environment and replace one or more of the integrated computational elements. This can represent a significant project expense, not to mention downtime needed for designing and fabricating the replacement integrated computational element(s).

Figure 1:
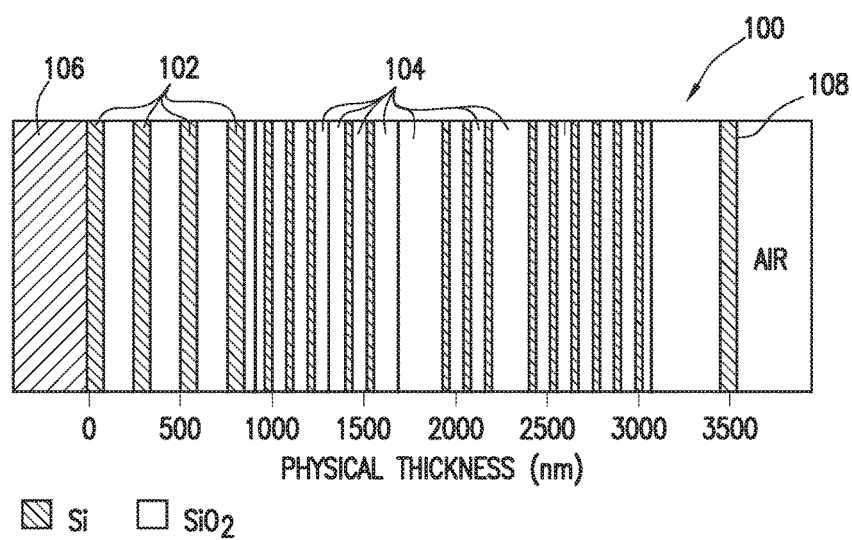
FIG. 1 is a diagram that illustrates a conventional design of an exemplary integrated computational element (ICE).

Before further discussing how integrated computational elements may be redesigned to address the foregoing issues, a brief discussion of conventional integrated computational element designs will first be provided. FIG. 1 is a diagram that illustrates a conventional design of an exemplary integrated computational element (ICE) 100. As illustrated, ICE 100 may include a plurality of alternating layers 102 and 104, such as silicon (Si) and $SiO_2$ (quartz), respectively. In general, layers 102 and 104 consist of materials whose index of refraction is high and low, respectively. Other examples may include niobia and niobium, germanium and germania, MgF, $SiO_x$, and other high and low index materials known in the art.

Layers 102 and 104 may be strategically deposited on optical substrate 106. As used herein, the term "optical substrate" will refer to a surface upon which layers 102 and 104 of an integrated computational element are deposited and which does not substantially optically interact with electromagnetic radiation over a wavelength range where a regression vector is being mimicked. That is, optical substrate 106 provides mechanical support for layers 102 and 104 and exhibits a substantially flat or known optical profile, such as an optical transmission profile, in the wavelength range over which ICE 100 is operational. In some embodiments, optical substrate 106 may be BK-7 optical glass. In other embodiments, optical substrate 106 may be another type of optical substrate, such as quartz, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like. Although some of the materials that may comprise optical substrate 106 are among those that may comprise layers 102 and 104, the layer thicknesses when used as optical substrate 106 are often much thicker. Opposite optical substrate 106, ICE 100 may include layer 108 that is generally exposed to the environment of the device or the sample undergoing analysis. Layer 108 may comprise the same material or a different material than optical substrate 106.

It should be understood that exemplary ICE 100 is not intended to be predictive for any particular characteristic of interest, but is provided for purposes of illustration only. Consequently, when analyzing for a particular characteristic of interest, the number of layers 102 and 104, their composition and their thicknesses may vary. Moreover, the materials that make up each layer 102 and 104 (e.g., Si and $SiO_2$) may vary, depending on the application, cost of materials, and/or applicability of the materials to the characteristic being monitored.

The number, thickness, and composition, for example, of layers 102 and 104 may be determined by performing a conventional spectroscopic analysis and then mimicking the regression vector for determining a characteristic of interest by iteratively processing the various layer parameters to best reproduce or "best fit" the regression vector. Additional details concerning how the regression vector is determined and its dot product is calculated are provided hereinbelow. A number of mathematical solutions may be obtained in best fitting the regression vector, and the various mathematical solutions may then be fabricated and further tested to determine if the ICE can indeed provide a suitable analysis of the characteristic of interest in practice. The regression vector being mimicked with ICE 100 typically includes any number of different wavelengths and may encompass one or more regions of the electromagnetic spectrum.

In some embodiments, the material of layers 102 and 104 may be doped or two or more materials may be combined in a manner to achieve a desired optical performance. In addition to solid layers, exemplary ICE 100 may also contain liquids and/or gases, optionally in combination with solids, in order to produce a desired optical performance. In the case of gases and liquids, ICE 100 may contain a corresponding vessel (not shown), which houses the gases or liquids.

The multiple layers 102 and 104 exhibit different refractive indices. By properly selecting the materials within layers 102 and 104, and the relative layer thicknesses and spacings, ICE 100 may be configured to selectively transmit, reflect, or refract predetermined fractions of electromagnetic radiation at different wavelengths. Each wavelength is given a predetermined weighting or loading factor. In this respect, ICE 100 essentially may function as an interference filter having a highly tailored optical performance. The thickness and spacing of layers 102 and 104 may be determined using a variety of approximation methods from a spectrum of a substance of interest. These methods may include inverse Fourier transform (IFT) of the optical transmission spectrum and structuring ICE 100 as the physical representation of the IFT. The approximations convert the IFT into a structure based on known materials with constant refractive indices.

The weightings that layers 102 and 104 of ICE 100 apply at each wavelength are set to the regression weightings described with respect to a known equation, data, or spectral signature. Briefly, ICE 100 may be configured to calculate the dot product of the input electromagnetic radiation into ICE 100 and a desired loaded regression vector represented by each layer 102 and 104 for each wavelength. The dot product is represented in the numerical output of a detector upon receipt of the electromagnetic radiation. As a result, the output intensity of the electromagnetic radiation from ICE 100 may be correlated to the characteristic of interest.

The present inventors discovered alternative configurations for integrated computational elements that are not based upon an architecture of alternating layers of materials to substantially mimic the regression vector of a sample characteristic. Namely, the inventors discovered that a quantum dot array may supplant the function of the alternating layers of materials found in conventional integrated computational elements. Instead of alternating layers of materials functioning as an interference filter in the integrated computational element, appropriate combinations of at least a portion of the quantum dots within the quantum dot array may produce a transmission profile that allows one to substantially mimic the regression vector for a characteristic of interest. Accordingly, by optically interacting electromagnetic radiation with at least a portion of the quantum dots in a quantum dot array, receiving the optically interacted electromagnetic radiation at a detector, and optionally applying an appropriate weighting to a signal received from the various quantum dots used in the analysis, a regression vector for the characteristic may be determined. Further details in this regard are provided below.

Integrated computational elements containing a quantum dot array can provide a number of distinct advantages compared to conventional integrated computational element architectures having alternating layers of materials with differing indices of refraction. Foremost, quantum dots having a wide range of spectral properties are now well known, and techniques for tailoring quantum dot syntheses to produce quantum dots with a particular size and/or surface coating are also well understood. Hence, quantum dots offer a wide breadth of spectral features that may be selected for mimicking the regression vector of a given sample characteristic. Indeed, depending on their composition, size and/or surface chemistry, quantum dots may have an absorption spectrum ranging from the deep ultraviolet to the mid-infrared region of the electromagnetic spectrum. Within the visible region of the electromagnetic spectrum, in particular, various quantum dots offer a wide range of spectral shapes and band positions that may be applied toward mimicking the regression vector for a sample characteristic.

Once a conventional integrated computational element has been fabricated in an effort to mimic the regression vector associated with a given sample characteristic, the integrated computational element's performance is fixed, although the outputs associated with various integrated computational elements may be combined with one another in order to alter their performance to some degree (e.g., computationally and/or by disposition of multiple integrated computational elements along an optical pathway). Nevertheless, if a conventional integrated computational element does not perform as intended, there may be little choice but to replace it, which can lead to excessive process downtime and expense. In contrast, when mimicking a regression vector using a quantum dot array, the quantum dots from various portions of the array can be combined in a multitude of ways to mimic the regression vector. The chosen subset of quantum dots need not necessarily be from contiguous regions of the quantum dot array. If a chosen subset of quantum dots within the array does not produce a desired result, a different subset of quantum dots can be applied in an attempt to obtain better results (e.g., better accuracy and/or sensitivity). Moreover, when mimicking the regression vector for a different sample characteristic, still another subset of quantum dots within the array may be applied. The number of set array positions may be made as large as necessary in order to achieve satisfactory analyses of a given type of sample and its characteristics. Hence, quantum dot arrays offer tremendous operational flexibility to be realized in mimicking regression vectors associated with one or more sample characteristics. This operational flexibility can be particularly beneficial in situations where a regression vector is complex and difficult to mimic using a multi-layered integrated computational element design. Further, sensitivity improvements may be much more readily realized using quantum dot arrays compared to that obtained with a physical or computational combination of multi-layered integrated computational element designs.

Although quantum dot arrays can contain an arbitrarily large number of set array positions in order to provide a sufficient breadth of quantum dots for substantially mimicking the regression vector of a sample characteristic, the arrays themselves may have a physical size that is still relatively small. Hence, the integrated computational elements of the present disclosure may be especially advantageous for deployment in confined locales where physical space is at a premium.

Moreover, the small physical size of quantum dot arrays can provide significant advantages in analyses where multiple conventional integrated computational elements are used to determine one or more sample characteristics. In the case of conventional integrated computational element architectures, multiple integrated computational elements can occupy more physical space than is available in a given operating environment. Operating mechanisms for moving multiple integrated computational elements into and out of an optical pathway can place further demands upon the available physical space, not to mention possible mechanical failure and electrical supply issues associated with such operating mechanisms. In contrast, at least in some embodiments, optical analysis tools containing an integrated computational element based upon a quantum dot architecture may contain no moving parts, such that all of the quantum dots reside within an optical pathway for exposure to electromagnetic radiation at the same time.

In various embodiments, optical analysis tools of the present disclosure can comprise: an electromagnetic radiation source that provides electromagnetic radiation to an optical pathway; an integrated computational element positioned at least partially within the optical pathway, the integrated computational element comprising a quantum dot array having a plurality of quantum dots disposed at a plurality of set array positions; and a detector that receives the electromagnetic radiation from the optical pathway after the electromagnetic radiation has optically interacted with the sample and the integrated computational element. The quantum dots located at one or more of the set array positions have spectral features such that optical interaction of the electromagnetic radiation with the quantum dots at the one or more set array positions substantially mimics a regression vector for at least one characteristic of a sample that also optically interacts with the electromagnetic radiation.

As used herein, the term "electromagnetic radiation" will refer to radio waves, microwave radiation, infrared and near-infrared radiation, visible light, ultraviolet light, X-ray radiation, gamma ray radiation, or any combination thereof. In more particular embodiments, the electromagnetic radiation that optically interacts with the integrated computational element may comprise infrared radiation having a wavelength range of about 1,000 nm to about 25,000 nm, or about 1,000 nm to about 20,000 nm, or about 1,000 nm to about 15,000 nm, or about 2,000 nm to about 10,000 nm, or about 2,000 nm to about 5,000 nm. In other more particular embodiments, the electromagnetic radiation that optically interacts with the integrated computational element may comprise ultraviolet and/or visible electromagnetic radiation having a wavelength range of 200 nm to about 1000 nm, or about 300 nm to about 800 nm, or about 400 nm to about 700 nm. In still other various embodiments, the electromagnetic radiation that optically interacts with the integrated computational element may span the ultraviolet, visible, and/or infrared regions, such as exemplary wavelength ranges of about 300 nm to about 3,000 nm, or about 400 nm to about 2,000 nm, or about 500 nm to about 1,000 nm. Fluorescent, phosphorescent, or blackbody emissions and/or the like from the sample may also be analyzed using an optical computing device.

As used herein, the term "optical pathway" will refer to the route along which electromagnetic radiation is transferred from a source to a detector. In the embodiments of the present disclosure, electromagnetic radiation optically interacts with a sample and an integrated computational element along the optical pathway.

As used herein, the term "optically interact" and grammatical variants thereof will refer to the reflection, transmission, scattering, diffraction, or absorption of electromagnetic radiation on, through, or from a sample or an integrated computational element. Accordingly, the term "optically interacted electromagnetic radiation" will refer to electromagnetic radiation that has been reflected, transmitted, scattered, diffracted, or absorbed by, emitted from, or re-radiated from a sample or an integrated computational element. In particular embodiments of the present disclosure, the electromagnetic radiation optically interacts with the integrated computational element containing a quantum dot array via transmission, and the transmitted electromagnetic radiation is subsequently received at a detector for analysis, as discussed hereinafter.

As used herein, the term "sample" or other variants thereof will refer to at least a portion of a substance of interest to be analyzed using an optical analysis tool containing an integrated computational element. It is to be understood that a sample need not necessarily represent a discrete aliquot of a bulk material. Rather, sampling of a bulk material may take place through a sampling window, wherein the bulk material may be static or flowing during the analysis.

In some embodiments, the sample being analyzed by the optical analysis tool may comprise a fluid. As used herein, the term "fluid" will refer to any substance that is capable of flowing, including particulate solids, liquids, gases, slurries, emulsions, powders, muds, glasses, any combination thereof, and the like. In some embodiments, the fluid can be an aqueous fluid, including water or the like. In some or other embodiments, the fluid can be a non-aqueous fluid, including organic compounds, more specifically, hydrocarbons, oil, a refined component of oil, petrochemical products, and the like. In some embodiments, the fluid can be a treatment fluid or a formation fluid. Other fluids can be analyzed similar and the foregoing fluids should not be considered limiting of the breadth of the present disclosure.

Accordingly, various downhole treatment operations may be observed by monitoring a treatment fluid or formation fluid using the optical computing devices disclosed herein. As used herein, the terms "treat," "treatment," "treating," and other grammatical variants thereof will refer to any operation that uses a fluid in conjunction with performing a desired function and/or for achieving a desired purpose. These terms do not imply any particular action by the fluid or any particular constituent thereof unless otherwise specified. Illustrative treatment operations that may be monitored using an integrated computational element of the present disclosure include, for example, drilling operations, fracturing operations, gravel packing operations, acidizing operations, scale dissolution and removal operations, consolidation operations, diverting operations, the like, and any combination thereof. A treatment fluid or a formation fluid may be monitored at any point during a treatment operation, including downhole within a subterranean wellbore. In further embodiments, feedback obtained from the optical analysis tool may allow a proactive change to be made in a treatment operation to change a particular condition in the subterranean wellbore.

In some or other embodiments, the sample being analyzed by the optical analysis tool may comprise a solid. Solids may include, for example, drill cuttings, wellbore surfaces, and the like. Again, one having ordinary skill in the art can envision other types of solids that may be analyzed in a related manner. In some embodiments, solids may be analyzed using electromagnetic radiation that is reflected from a sample and is subsequently conveyed for processing to an integrated computational element comprising a quantum dot array, as described herein.

As used herein, the term "quantum dot array" will refer to a geometric arrangement of different types of quantum dots disposed at a plurality of set (discrete) array positions, where spectral properties of the quantum dots at each set array position are known and distinct. The particular geometric arrangement of the array positions is not considered to be especially limited.

As used herein, term "quantum dot" will refer to any semiconductor nanoparticle which is less than about 1 micron in size. The larger a semiconductor nanoparticle is, the longer the wavelength of electromagnetic radiation that it will effectively optically interact with. In some embodiments, the quantum dots may have a size ranging between about 1 nm and about 10 nm. Such quantum dots may optically interact with visible electromagnetic radiation. In some embodiments, the quantum dots may have an upper size limit of about 1 micron. Factors that may be considered when choosing the sizes of the quantum dots in the quantum dot array may include, for example, the wavelength of the electromagnetic radiation, the size of the detector and/or each pixel in an array detector, the number of analytes of interest, and the like.

As used herein, the term "substantially mimic" will refer to the degree of shape similarity between the transmission function of an integrated computational element and a given regression vector. In various embodiments, a regression vector can be considered to be substantially mimicked, if the degree of shape similarity is at least about 90%. It is to be recognized, however, that some application and analytes may require a higher or lower degree of shape similarity. Such considerations may vary from application to application and lie within the purview of one having ordinary skill in the art.

The optical analysis tools and related methods of the present disclosure utilize an integrated computational element to substantially mimic a regression vector for a sample characteristic and then calculate a dot product of the regression vector to determine a value for the characteristic. As one of ordinary skill in the art will recognize, a dot product of a vector is a scalar quantity (i.e., a real number). While the dot product value is believed to have no physical meaning by itself (it may be positive or negative and of any magnitude), comparison of a sample dot product value with dot product values obtained for known reference standards may allow the sample dot product value to be correlated with a characteristic's magnitude, thereby allowing unknown samples to be analyzed. To determine the dot product, one simply multiplies the regression coefficient for the regression vector at a given wavelength by the spectral intensity at the same wavelength. This process is repeated for all wavelengths over the wavelength range being analyzed, and the products are summed to yield the dot product.

Further details regarding the determination of a regression vector and its use in determining a dot product are now provided. It is possible to derive information from electromagnetic radiation optically interacting with a sample by, for example, separating the electromagnetic radiation from several samples into wavelength bands and performing a multiple linear regression of the band intensity against a characteristic's value determined by another measurement technique for each sample. The measured characteristic may be expressed and modeled by multiple linear regression techniques that will be familiar to one having ordinary skill in the art. Specifically, if y is the measured value of a given characteristic, y may be expressed as in Formula 1, $$y = a_0 + a_1 w_1 + a_2 w_2 + a_3 w_3 + a_4 w_4 + \ldots \quad \text{(Formula 1)}$$

where each a is a constant determined by the regression analysis and each w is the intensity for each wavelength band. Depending on the circumstances, the estimate obtained from Formula 1 may be inaccurate, for example, due to the presence of other constituents within the sample that may affect the intensity of the wavelength bands.

A more accurate estimate may be obtained by expressing the electromagnetic radiation in terms of its principal components. To obtain the principal components, spectroscopic data is collected for a variety of similar samples using the same type of electromagnetic radiation. Following exposure to each sample, the electromagnetic radiation may be collected and the spectral intensity at each wavelength may be measured. This data may then be pooled and subjected to a linear-algebraic process known as singular value decomposition (SVD) in order to determine the principal components. Use of SVD in principal component analysis will be well understood by one having ordinary skill in the art. Briefly, principal component analysis is a dimension reduction technique, which takes m spectra with n independent variables and constructs a new set of eigenvectors that are linear combinations of the original variables. The eigenvectors may be considered a new set of plotting axes. The primary axis, termed the first principal component, is the vector that describes most of the data variability. Subsequent principal components describe successively less sample variability, until the higher order principal components essentially describe only spectral noise. Use of too few principal components may provide an inaccurate estimate, whereas use of too many principal components may unduly model spectral noise.

Typically, the principal components are determined as normalized vectors. Thus, each component of an electromagnetic radiation sample may be expressed as $x_n z_n$, where $x_n$ is a scalar multiplier and $z_n$ is the normalized component vector for the $n_{th}$ component. That is, $z_n$ is a vector in a multi-dimensional space where each wavelength is a dimension. As will be understood by one having ordinary skill in the art, normalization determines values for a component at each wavelength so that the component maintains its shape and the length of the principal component vector is equal to one. Thus, each normalized component vector has a shape and a magnitude so that the components may be used as the basic building blocks of any electromagnetic radiation sample having those principal components. Accordingly, each electromagnetic radiation sample may be described by a combination of the normalized principal components multiplied by the appropriate scalar multipliers, as set forth in Formula 2.

$$x_1z_1+x_2z_2+\ldots+x_nz_n \quad \text{(Formula 2)}$$

The scalar multipliers $x_n$ may be considered the "magnitudes" of the principal components in a given electromagnetic radiation sample when the principal components are understood to have a standardized magnitude as provided by normalization. Because the principal components are orthogonal, they may be used in a relatively straightforward mathematical procedure to decompose an electromagnetic radiation sample into the component magnitudes, which may accurately describe the data in the original electromagnetic radiation sample. Since the original electromagnetic radiation sample may also be considered a vector in the multi-dimensional wavelength space, the dot product of the original signal vector with a principal component vector is the magnitude of the original signal in the direction of the normalized component vector. That is, it is the magnitude of the normalized principal component present in the original signal. This is analogous to breaking a vector in a three-dimensional Cartesian space into its X, Y and Z components. The dot product of the three-dimensional vector with each axis vector, assuming each axis vector has a magnitude of 1, gives the magnitude of the three dimensional vector in each of the three directions. The dot product of the original signal and some other vector that is not perpendicular to the other three dimensions provides redundant data, since this magnitude is already contributed by two or more of the orthogonal axes.

Because the principal components are orthogonal (i.e., perpendicular) to each other, the dot product of any principal component with any other principal component is zero. Physically, this means that the components do not interfere with each other. If data is altered to change the magnitude of one component in the original electromagnetic radiation signal, the other components remain unchanged. In the analogous Cartesian example, reduction of the X component of the three-dimensional vector does not affect the magnitudes of the Y and Z components.

Principal component analysis provides the fewest orthogonal components that can accurately describe the data carried by the electromagnetic radiation samples. Thus, in a mathematical sense, the principal components are components of the original electromagnetic radiation that do not interfere with each other and that represent the most compact description of the spectral signal. Physically, each principal component is an electromagnetic radiation signal that forms a part of the original electromagnetic radiation signal. Each principal component has a shape over some wavelength range within the original wavelength range. Summing the principal components may produce the original signal, provided each component has the proper magnitude.

The principal components may comprise a compression of the information carried by the total light signal. In a physical sense, the shape and wavelength range of the principal components describe what information is in the total electromagnetic radiation signal, and the magnitude of each component describes how much of that information is present. If several electromagnetic radiation samples contain the same types of information, but in differing amounts, then a single set of principal components may be used to describe (except for noise) each electromagnetic radiation sample by applying appropriate magnitudes to the components. The principal components may be used to provide an estimate of a sample characteristic based upon the information carried by electromagnetic radiation that has optically interacted with the sample. Differences observed in the spectra of samples having varying values of a characteristic may be described as differences in the magnitudes of the principal components. Thus, the value of a characteristic may be expressed by the principal components according to Formula 3 in the case where 4 principal components are used, $$y=a_0+a_1x_1+a_2x_2+a_3x_3+a_4x_4 \quad \text{(Formula 3)}$$

where y is a concentration of a constituent or value of a characteristic, each a is a constant determined by the regression analysis, and $x_1$, $x_2$, $x_3$ and $x_4$ are the first, second, third, and fourth principal component magnitudes, respectively. Formula 3 may be referred to as a regression vector. The regression vector may be used to provide an estimate for the value of a characteristic for an unknown sample.

Using Formula 3, a computer may read spectral intensity data and decompose the electromagnetic radiation sample into the principal component magnitudes $x_n$ by determining the dot product of the total signal with each component. The component magnitudes are then applied to the regression equation to determine a value of a characteristic.

To simplify the foregoing procedure, however, the regression vector may be converted to a form that is a function of wavelength so that only one dot product is determined. Each normalized principal component vector $z_n$ has a value over all or part of the total wavelength range. If each wavelength value of each component vector is multiplied by the regression constant $a_n$ corresponding to the component vector, and if the resulting weighted principal components are summed by wavelength, the regression vector takes the form of Formula 4, $$y=a_0+b_1u_1+b_2u_2+\ldots+b_nu_n \quad \text{(Formula 4)}$$

where $a_0$ is the first regression constant from Formula 3, $b_n$ is the sum of the multiple of each regression constant $a_n$ from Formula 3 and the value of its respective normalized regression vector at wavelength n, and $u_n$ is the intensity of the electromagnetic radiation at wavelength n. Thus, the new constants define a vector in wavelength space that directly describes the value of a characteristic of a sample. The regression vector in the form of Formula 4 represents the dot product of an electromagnetic radiation sample with this vector.

Normalization of the principal components provides the components with an arbitrary value for use during the regression analysis. Accordingly, it is very unlikely that the observed dot product value produced by the regression vector will be equal to the actual value of characteristic within a sample. The dot product result is, however, a function of the characteristic's value. As discussed above, the function may be determined by measuring one or more known calibration samples by conventional means and comparing the result to the dot product value of the regression vector. Thereafter, the dot product result can be compared to the value obtained from the calibration standards in order to determine the characteristic of an unknown sample. The function relating the dot product to the characteristic may be of any type including, for example, linear functions, quadratic functions, polynomial functions, logarithmic functions, exponential functions, and the like.

In some embodiments, principal component analysis techniques may include partial least squares analysis, for example. The principal component analysis may be conducted using standard statistical analysis software packages including, for example, XL Stat for MICROSOFT®

EXCEL®, the UNSCRAMBLER® from CAMO Software, and MATLAB® from MATHWORKS®).

In various embodiments, determination of a regression vector and calculation of a dot product may take place under computer control or another type of automated processing means. Further, as described below, in some embodiments, modifications to a process may take place to change the value of a characteristic once it has been determined. Such processes may also take place under computer control, optionally using an artificial neural network.

It is to be recognized that in the various embodiments herein taking place under computer control or other automated processing means, various blocks, modules, elements, components, methods, and algorithms can be implemented through using computer hardware, software and combinations thereof. To illustrate this interchangeability of hardware and software, various illustrative blocks, modules, elements, components, methods and algorithms have been described generally in terms of their functionality. Whether such functionality is implemented as hardware or software will depend upon the particular application and any imposed design constraints. For at least this reason, it is to be recognized that one of ordinary skill in the art can implement the described functionality in a variety of ways for a particular application. Further, various components and blocks can be arranged in a different order or partitioned differently, for example, without departing from the spirit and scope of the embodiments expressly described.

Computer hardware used to implement the various illustrative blocks, modules, elements, components, methods and algorithms described herein can include a processor configured to execute one or more sequences of instructions, programming, or code stored on a readable medium. The processor can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network or any like suitable entity that can perform calculations or other manipulations of data. In some embodiments, computer hardware can further include elements such as, for example, a memory [e.g., random access memory (RAM), flash memory, read only memory (ROM), programmable read only memory (PROM), erasable PROM], registers, hard disks, removable disks, CD-ROMs, DVDs, or any other like suitable storage device.

Executable sequences described herein can be implemented with one or more sequences of code contained in a memory. In some embodiments, such code can be read into the memory from another machine-readable medium. Execution of the sequences of instructions contained in the memory can cause a processor to perform the process steps described herein. One or more processors in a multi-processing arrangement can also be employed to execute instruction sequences in the memory. In addition, hard-wired circuitry can be used in place of or in combination with software instructions to implement various embodiments described herein. Thus, the present embodiments are not limited to any specific combination of hardware and software.

As used herein, a machine-readable medium will refer to any medium that directly or indirectly provides instructions to a processor for execution. A machine-0readable medium can take on many forms including, for example, non-volatile media, volatile media, and transmission media. Non-volatile media can include, for example, optical and magnetic disks. Volatile media can include, for example, dynamic memory. Transmission media can include, for example, coaxial cables, wire, fiber optics, and wires that form a bus. Common forms of machine-readable media can include, for example, floppy disks, flexible disks, hard disks, magnetic tapes, other like magnetic media, CD-ROMs, DVDs, other like optical media, punch cards, paper tapes and like physical media with patterned holes, RAM, ROM, PROM, EPROM and flash EPROM.

Figure 2:
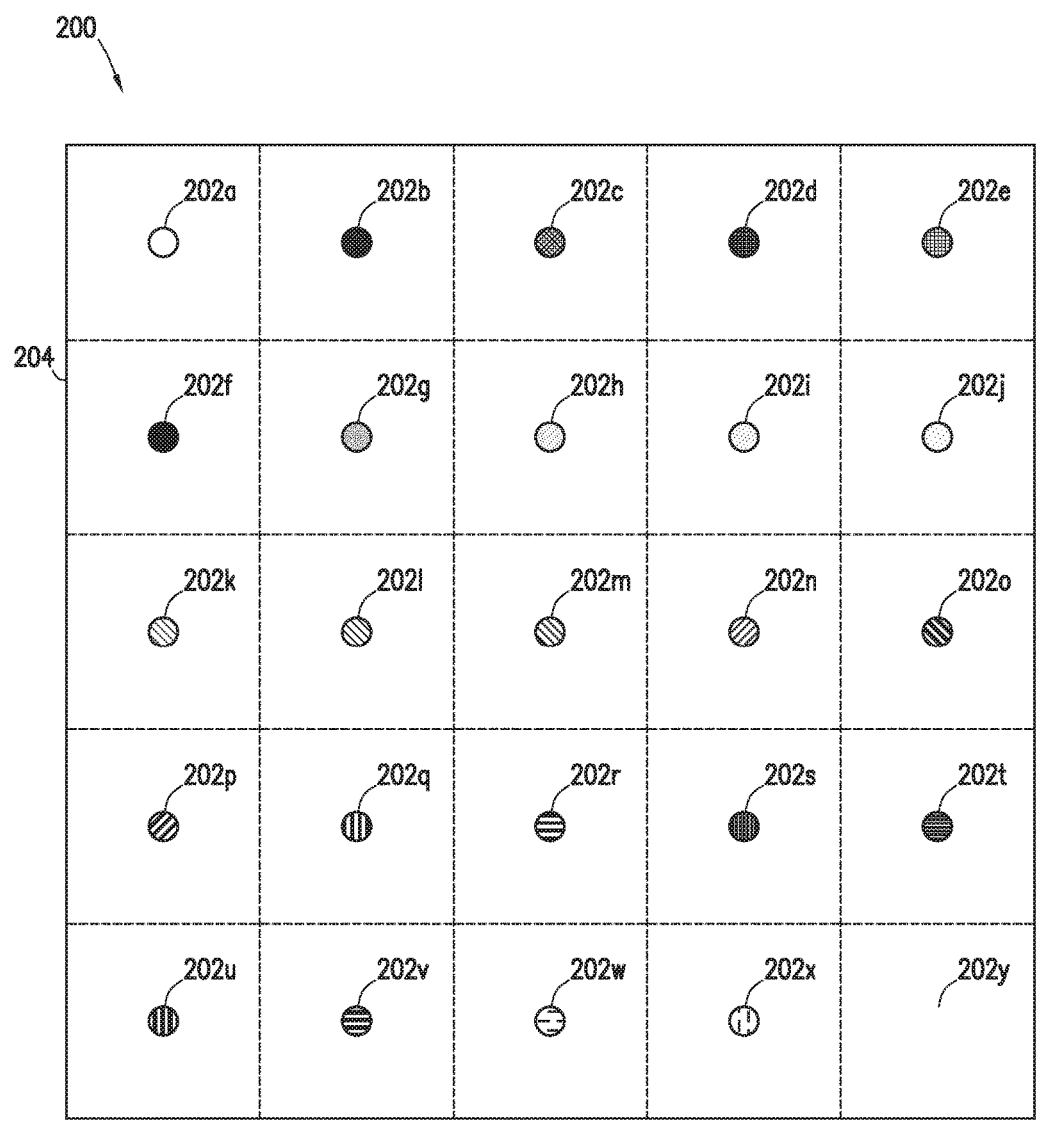
FIG. 2 shows a diagram of an illustrative quantum dot array containing a plurality of quantum dots at a plurality of set array positions.

Turning now to the integrated computational elements themselves, FIG. 2 shows a diagram of an illustrative quantum dot array containing a plurality of quantum dots at a plurality of set array positions. As shown in FIG. 2, quantum dot array 200 is a 5×5 array containing quantum dots located at set array positions 202a-202x upon substrate 204. Substrate 204 may be formed from any suitable material, such as the illustrative optical substrate materials described hereinabove in regard to FIG. 1. The quantum dots located at each of set array positions 202a-202x are different and have spectral properties differing from those in other set array positions within quantum dot array 200. Accordingly, illustrative quantum dot array 200 has at least 24 unique spectral features which may be combined in various combinations and weightings to substantially mimic the regression vector of a sample characteristic.

FIG. 2 also shows that quantum dot array 200 may optionally contain at least one set array positon that lacks quantum dots. Specifically, in illustrative quantum dot array 200, set array position 202y contains no quantum dots. The electromagnetic radiation transmitted through set array position 202y and received at a detector (see below) may, in non-limiting embodiments, be used to correct for variation in the intensity of the electromagnetic radiation source and/or to account for drift in the detector performance as a function of temperature or other operating conditions. Further disclosure in this regard follows hereinbelow. In other embodiments consistent with the present disclosure, however, all of the set array positions may contain quantum dots, thereby adding an additional spectral feature that may be used in mimicking the regression vector for a sample characteristic. In this case, alternative techniques for addressing variations in detector performance may be employed.

Although FIG. 2 has shown a 5×5 array of quantum dots, it is to be recognized that this is for purposes of illustration and not limitation. The quantum dot array can be made arbitrarily large in order to accommodate a sufficient number of quantum dots having distinct spectral features for substantially mimicking one or more regression vectors for various sample characteristics. The number of set array positions can be determined, for example, based upon the complexity of the regression vector(s) to be mimicked and the spectral features of the quantum dots one has on hand or that can be produced synthetically. In some embodiments, the quantum dot array can contain at least 2 set array positions containing quantum dots. In more particular embodiments, a number of set array positions in the quantum dot array can be at least about 10, or at least about 20, or at least about 50, or at least about 100, or at least about 200, or at least about 500, or at least about 1,000. In still more particular embodiments, a number of set array positions in the quantum dot array can range between about 20 and about 1,000, or between about 50 and about 500, or between about 75 and about 250, or between about 100 and about 200. A number of quantum dots within the quantum dot array may be dictated by the number of detection channels that are available in the array detector.

In order to direct a sufficient number of photons to each set array position, collimating optics may be present within the optical pathway between the electromagnetic radiation source and the detector. The collimating optics may be present at any location along the optical pathway. Suitable collimating optics for use within the optical pathway will be familiar to one having ordinary skill in the art and may include mirrors and various types of lenses (e.g., convex lenses, Fresnel lenses, and combinations thereof).

Furthermore, although FIG. 2 has depicted the quantum dot array as a square array, it is to be recognized that the disposition of the set array positions is not limited to this particular configuration. That is, the number of vertical and horizontal elements within the quantum dot array need not necessarily be equal, although they may be in order to minimize the array's operational footprint. In other various embodiments, the quantum dot array may have the set array positions disposed linearly, rectangularly, circularly, or any other regular geometric disposition. All that needs to be known about the array is the particular types of quantum dots that are present at the various set array positions and their corresponding spectral properties. Random geometric dispositions of the set array positions may also be used, again provided that the array can be effectively mapped to determine the particular types of quantum dots present at various array positions and their spectral features.

Figure 3:
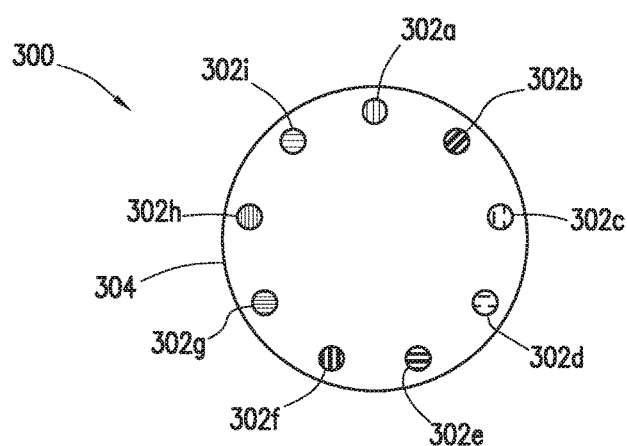
FIG. 3 shows a diagram of an illustrative circular quantum dot array containing a plurality of quantum dots at a plurality of set array positions.

For example, FIG. 3 shows a diagram of an illustrative circular quantum dot array containing a plurality of quantum dots at a plurality of set array positions.

Quantum dot array 300 contains set array positions 302a-302g upon substrate 304, where each of the set array positions contain quantum dots having different spectral features. Again, the number of set array positions and types of quantum dots housed thereon is arbitrary. A set array position lacking quantum dots may also be present (not shown in FIG. 3).

In some embodiments, a quantum dot array may be rotated to expose only one of the set array positions to electromagnetic radiation at a time. That is, in such embodiments, only a portion of the quantum dot array lies within the optical pathway at a given point in time and the quantum dots are thereby exposed sequentially to the electromagnetic radiation. Upon optically interacting with the quantum dots at each array position chosen for use in mimicking a regression vector, the electromagnetic radiation can be transmitted to a detector for collection and subsequent processing of the individual signals. That is, the detector output from the chosen array positions may be computationally combined to substantially mimic the regression vector as described elsewhere herein. Although a circular quantum dot array may be particularly convenient for sequential exposure of quantum dots to electromagnetic radiation via rotational motion, it is to be recognized that sequential exposure may also take place in other ways, such as through translational x-y motion of a quantum dot array similar to that shown in FIG. 2.

The electromagnetic radiation source providing electromagnetic radiation to the optical analysis tools of the present disclosure is not considered to be particularly limited. Illustrative electromagnetic radiation sources may include, for example, a light bulb or other filament-based source, a light emitting device (LED), a laser, a blackbody, a photonic crystal, an X-Ray source, a gamma ray source, combinations thereof, or the like.

In some embodiments, the electromagnetic radiation source may be a planar, thermal blackbody emitter. Planar, thermal blackbody emitters may be resistively heated under low-power conditions to produce a broad wavelength distribution of emitted electromagnetic radiation. Suitable planar, thermal blackbody emitters include, but are not limited to, those available from Intex (Pordenone, Italy), such as exemplary product numbers INTX 22-1000, INTX 17-0900 and INTX 08-0300. These planar, thermal blackbody emitters provide a distribution of emitted wavelengths over a range of about 1-20 microns upon resistive heating, with the predominant emitted wavelengths falling near 3 microns and varying in position to some degree depending upon the actual heating temperature. Not only are planar, thermal blackbody emitters low-power devices, but they are also resistant to thermal and environmental degradation, collectively making them well suited for use downhole and in other harsh sampling environments. Planar, thermal blackbody emitters are also small in size, thereby further facilitating miniaturization of optical computing devices.

Even more advantageously, planar, thermal blackbody emitters are capable of stable pulsed operation up to a frequency of about 150 Hz, which allows the electromagnetic radiation provided within an optical pathway to be chopped by virtue of the source's operation, rather than by employing a mechanical chopper to improve detection sensitivity. In contrast, filament-based electromagnetic radiation sources are believed to be unsuitable for being stably pulsed in this manner. Hence, use of a planar, thermal blackbody emitter can allow further reductions in operational profile to be realized by allowing a mechanical chopper to be omitted from the optical pathway of the presently described optical analysis tools.

Because a broad spectrum of wavelengths is produced by planar, thermal blackbody emitters, it may be beneficial to employ optical bandpass filters in conjunction with the planar array detector, thereby allowing only a desired subset of emitted wavelengths to pass to the detector after optically interacting with the integrated computational element. Even when optical bandpass filters are incorporated in the optical pathway, they do not significantly increase the operational profile, thereby maintaining the advantages discussed hereinabove. Suitable optical bandpass filters can be identified by one having ordinary skill in the art.

As indicated above, electromagnetic radiation may be received at a detector after sequentially exposing the quantum dots within at least a portion of the set array positions to the electromagnetic radiation. Translational and/or rotational motion of the quantum dot array may be used for this purpose. Illustrative detectors that may be used in conjunction with such embodiments include, for example, thermal detectors such as a thermopile or photoacoustic detectors, semiconductor detectors, piezoelectric detectors, photon detectors (such as a photomultiplier tube), photodiode detectors, or the like. Other types of detectors will be familiar to one having ordinary skill in the art.

In some embodiments, the detector may comprise an array detector that receives electromagnetic radiation simultaneously from each of the set array positions. As used herein, the term "array detector" will refer to a photosensitive device having at least two detection regions that are laterally spaced apart from one another in an x-y coordinate plane. The optical detection regions are responsive to an input of photons thereon and may also be sensitive to the surrounding temperature conditions. A blank detection region that is not exposed to electromagnetic radiation may also be present in order to provide a correction factor for thermal variations in the array detector's response, as discussed further below. Illustrative array detectors may include, for example, charge coupled device (CCD) detectors, photodiode array detectors, pixel and hybrid pixel array detectors, split detectors, or the like. In more specific embodiments, the array detector may have at least as many detection channels or detection regions as the quantum dot array has set array positions. That is, for each set array position, there is a corresponding detection channel or detection region within the array detector for collecting electromagnetic radiation that has optically interacted with the associated quantum dots. Thus, array detectors may collect and individually process electromagnetic radiation that has optically interacted with the quantum dots at each of the set array positions in order to determine a sample characteristic based upon a regression vector.

As mentioned above, the quantum dots at each of the set array positions can be utilized in mimicking a regression vector corresponding to a sample characteristic. However, more desirably, less than all of the quantum dots within the quantum dot array are used for this purpose. That is, in some embodiments, optical interaction of the electromagnetic radiation with the quantum dots from less than all of the set array positions may mimic the regression vector for the at least one characteristic of the sample. As indicated above, the number of quantum dots necessary to substantially mimic the regression vector may vary depending upon a number of factors, such as the complexity of the regression vector and the breadth of the spectral features present in the quantum dots within the quantum dot array. Accordingly, by acquiring transmission spectra associated with the quantum dots in each of the set array positions and processing the spectral data from only a portion of these quantum dots, the regression vector may still be satisfactorily mimicked. Moreover, by processing the spectral data from only a portion of the quantum dots, greater flexibility may be realized in mimicking the regression vector and determining a sample characteristic than if all the spectral data is processed. That is, if the original subset of quantum dots chosen for processing to substantially mimic the regression vector is unsatisfactory, a different subset of the quantum dots within the quantum dot array may be chosen and processed to provide a more accurate portrayal of the regression vector associated with a sample characteristic.

For example and by way of illustration only, referring again to FIG. 2, a regression vector may be substantially mimicked by combining the detector outputs associated with the quantum dots at each of set array positions $202a$-$202e$. If this combination of quantum dots does not result in the regression vector being mimicked with a sufficient degree of accuracy, quantum dots from additional set array positions may be added to the original subset of quantum dots (e.g., adding the quantum dots from set array positions $202f$-$202j$ or some other subset of the quantum dots) or by replacing at least a portion of the original subset of quantum dots with those from an entirely different subset of set array positions (e.g., set array positions $202k$-$202o$ or $202p$, $202q$, $202u$ and $202v$). Again, the chosen subset of set array positions may be chosen such that the quantum dots have a sufficient breadth of spectral features to substantially mimic a given regression vector.

When less than all of the quantum dots are used to substantially mimic the regression vector, the detector may still receive electromagnetic radiation that has optically interacted with the quantum dots at each of the set array positions and only process the acquired data from a portion of the array positions (i.e., the array positions having quantum dots that may be used to substantially mimic the regression vector). That is, the optical analysis tool may be configured to disregard electromagnetic radiation received at the detector from any of the set array positions containing quantum dots that are not used to substantially mimic the regression vector upon their optical interaction with electromagnetic radiation. The optical analysis tool may be configured to disregard selected data received from the quantum dots by only processing the data from certain detection channels of an array detector, for example. Optionally, this action may take place offline after the data has been collected and stored. In alternative embodiments in which a non-array detector is used, data may be received individually from the quantum dots and stored in an appropriate storage medium for offline processing using only the spectral data from a selected subset of the fixed array positions.

In still other alternative embodiments, an optical analysis tool may be configured to disregard electromagnetic radiation that has optically interacted with some of the quantum dots by blocking the optical pathway between the unused quantum dots and the detector. Techniques suitable for blocking the optical pathway will be familiar to one having ordinary skill in the art. For example, blocking the optical pathway may involve the placement of optical filters configured to attenuate certain wavelengths of electromagnetic radiation, or an absorbing barrier may be physically placed in at least a portion of the optical pathway.

Regardless of how the spectral data from the quantum dots at the various set array positions is acquired and stored, the optical analysis tool may be configured to computationally combine a plurality of signals from the detector corresponding to electromagnetic radiation received from quantum dots at each of the one or more set array positions used to mimic the regression vector. The process of computationally combining the signals may involve, for example, adding the signals in a linear combination with an appropriate weighting factor being applied.

As indicated above, the quantum dot arrays of the present disclosure may, in some embodiments, contain a subset of quantum dots at the set array positions that are sufficient to mimic the regression vectors for multiple characteristics of a sample. Accordingly, in some embodiments, optical interaction of the electromagnetic radiation with the quantum dots in a first plurality of the set array positions can substantially mimic a regression vector for a first characteristic of a sample, and optical interaction of the electromagnetic radiation with the quantum dots in a second plurality of the set array positions can substantially mimic a regression vector for a second characteristic of the sample. The first and second characteristics differ from one another and are related to different physical properties of sample. In some embodiments, the first plurality of the set array positions and the second plurality of set array position used in substantially mimicking the two regression vectors may also differ from one another. That is, different subsets of quantum dots may be used to mimic the regression vectors for different sample characteristics. It is to be recognized, however, that quantum dots from certain set array positions may be common to both groups. In other embodiments, the two groups may be entirely distinct with no quantum dots in common. Moreover, in still other alternative embodiments, the same subset of quantum dots may also be used to substantially mimic the regression vector for the first and second characteristics if the spectral data is processed differently (i.e., different computational combinations). The regression vectors for the first and second sample characteristics may be similar in shape, or they may be entirely different in shape.

When analyzing the characteristics of a sample using an optical analysis tool containing an integrated computational element of the present disclosure, the integrated computational element and the detector may abut one another or they may be spaced apart. The electromagnetic radiation may optically interact with the sample before optically interacting with the integrated computational element, or it may optically interact afterward. When the integrated computational element is abutted with the detector, the sample may optically interact with the electromagnetic radiation first. However, when the integrated computational element and the detector are spaced apart, the sample may optically interact with the electromagnetic radiation before or after the electromagnetic radiation has optically interacted with the integrated computational element. Abutted configurations for the integrated computational element and the detector may be particularly desirable in order to minimize the operational footprint of the optical analysis tool by shortening the optical pathway along which the electromagnetic radiation travels. In embodiments where an array detector is used, each of the set array positions in the quantum dot array may have a corresponding optical detection region in the detector.

Figure 4:
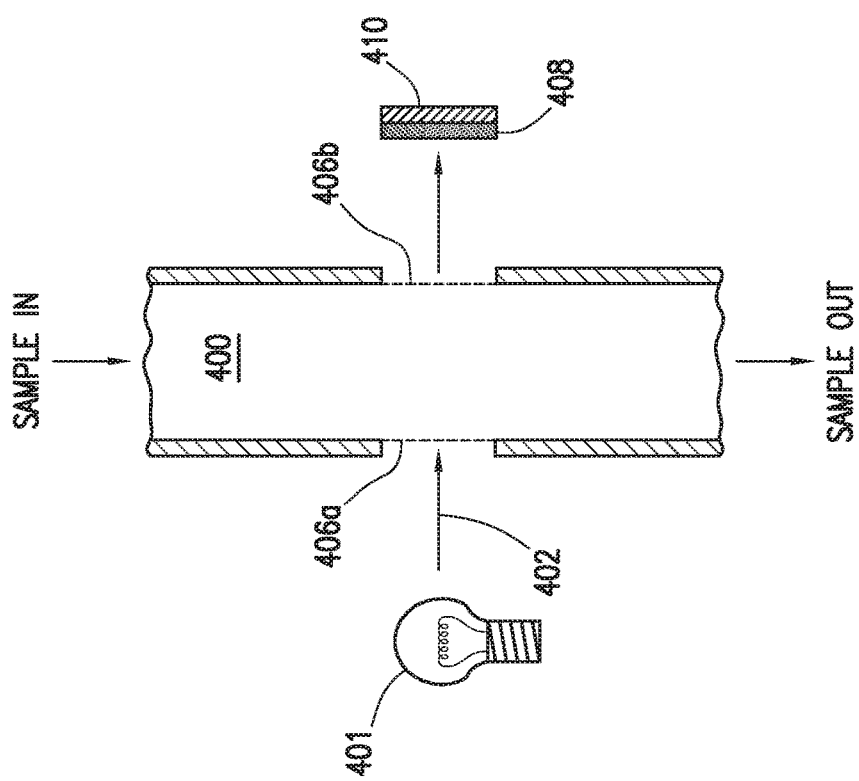
FIG. 4 shows a diagram of an illustrative optical analysis tool configuration in which an integrated computational element containing a quantum dot array is abutted against an array detector.

FIG. 4 shows a diagram of an illustrative optical analysis tool configuration in which an integrated computational element containing a quantum dot array is abutted against an array detector. As shown in FIG. 4, electromagnetic radiation source 401 supplies electromagnetic radiation 402 to a sample within sample chamber 400. The sample may be static or flowing in sample chamber 400 when undergoing analysis. Electromagnetic radiation 402 enters sample chamber 400 via window 406a and exits via window 406b. Upon exiting window 406b, electromagnetic radiation 402 carries information about the sample and optically interacts with a quantum dot array within integrated computational element 408, which is abutted against array detector 410. As discussed above, integrated computational element 408 may contain spectroscopically distinct quantum dots within a sufficient number of set array positions to substantially mimic a regression vector for a characteristic of the sample. Array detector 410 may have a corresponding number of detection elements or channels for processing electromagnetic radiation 402 that is received after optically interacting with the sample and the quantum dots within integrated computational element 408.

Figure 5:
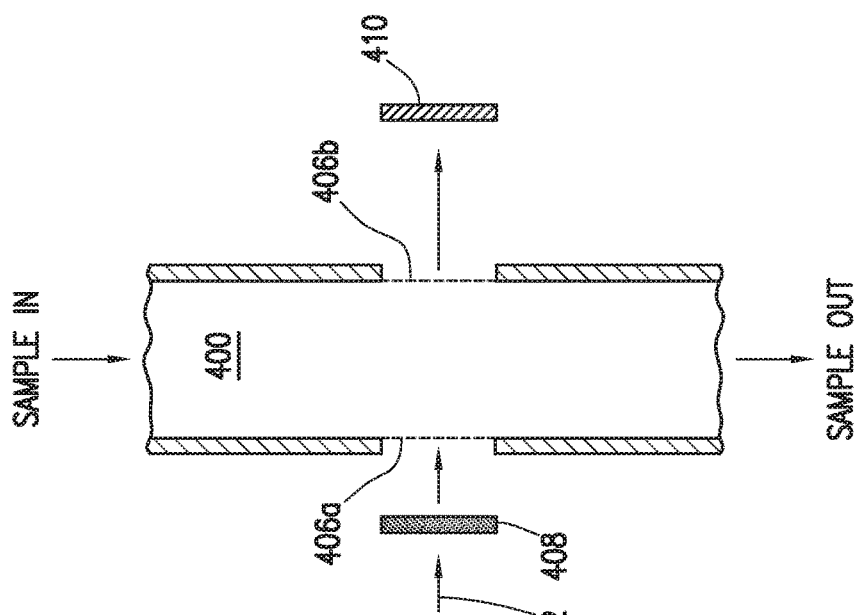
FIG. 5 shows a diagram of an illustrative optical analysis tool configuration in which an integrated computational element and an array detector are spaced apart.

Although FIG. 4 has shown integrated computational element 408 and array detector 410 abutted together, they also may be spaced apart as shown in FIG. 5. FIG. 5 shows a diagram of an illustrative optical analysis tool configuration in which an integrated computational element and an array detector are spaced apart. When spaced apart from array detector 410, integrated computational element 408 may be placed at any point along the optical pathway. As illustrated in FIG. 5, integrated computational element 408 is placed at a location before electromagnetic radiation 402 enters window 406a. However, it may be equivalently placed at a location after electromagnetic radiation 402 exits window 406b as well.

Figure 6:
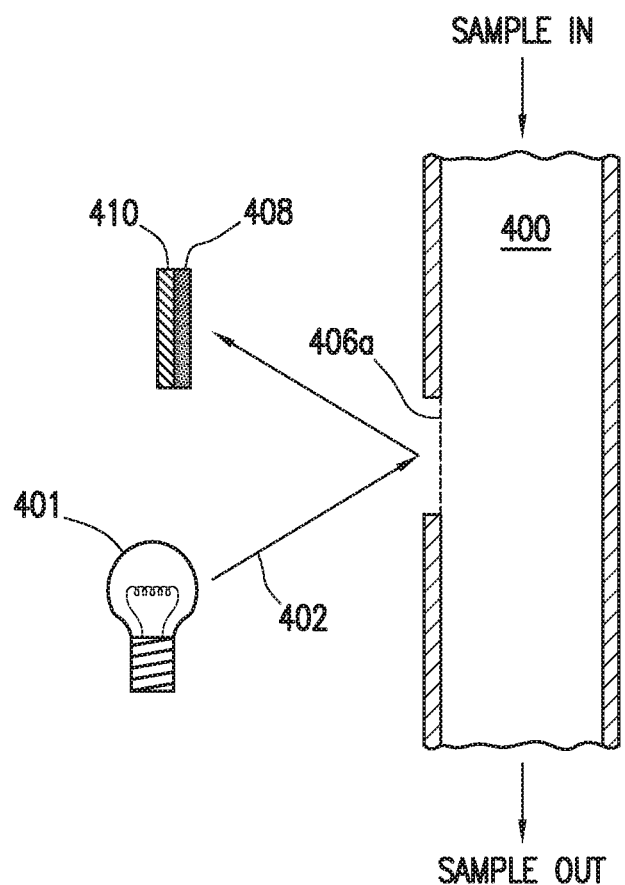
FIG. 6 shows a diagram of an illustrative optical analysis tool configuration in which electromagnetic radiation optically interacts with a sample by reflection before conveyance to an integrated computational element and an array detector.

Similarly, although FIGS. 4 and 5 have shown electromagnetic radiation 402 being transmitted through sample chamber 400, reflective configurations are also possible, as illustrated in FIG. 6. FIG. 6 shows a diagram of an illustrative optical analysis tool configuration in which electromagnetic radiation optically interacts with a sample by reflection before conveyance to an integrated computational element and an array detector. Although FIG. 6 has depicted integrated computational element 408 and array detector 410 in an abutted configuration, related configurations in which they are spaced apart are also consistent with the embodiments of the present disclosure.

In some embodiments of the present disclosure, the quantum dot array may contain at least one open set array position that lacks quantum dots (for example, see FIG. 2). The electromagnetic radiation received at the detector that has optically interacted with this array position represents that which has optically interacted with the sample but has not undergone further processing with quantum dots. Accordingly, electromagnetic radiation reaching the detector from this open set array position may be used to normalize the response of the other signals (i.e., the detector signals produced by optically interacting electromagnetic radiation with both a sample and quantum dots), and/or to account for variations in the intensity of the output of the electromagnetic radiation source. Thermal variations in the detector may also be accounted for. For example, the electromagnetic radiation reaching an array detector from an open set array position of a quantum dot array may be used to account for thermal variation the other detection channels of the array detector.

In some or other embodiments, an array detector may comprise a blank detection region (i.e., detection channel) that is not exposed to electromagnetic radiation. By blocking a detection channel of an array detector from receiving incident photons, the detection channel may serve as a blank detection region since any response that it produces is substantially due to thermal effects. Accordingly, a blank detection region may be used to normalize for thermal variance in the detector performance.

Any type of quantum dot may be used in constructing the quantum dot arrays of the presently described integrated computational elements. As discussed above, a multitude of quantum dots having a range of compositions, sizes, surface coatings and the like are accessible synthetically or available commercially. These parameters may be independently varied to modulate the optical performance of the quantum dots. The breadth of quantum dots chosen for inclusion in the quantum dot array may be such that a sufficient number of distinct types of quantum dots are present at the set array positions to substantially mimic the regression vector of a sample characteristic. The spectral properties of the quantum dots may be selected such that the optical analysis tool is operative over a desired wavelength range.

Accordingly, quantum dots suitable for inclusion in the quantum dot arrays of the present disclosure are not seen to be particularly limited. Illustrative but non-limiting semiconductor materials that may be processed as quantum dots include, for example, lead sulfide, lead selenide, cadmium selenide, cadmium sulfide, cadmium telluride, indium arsenide, indium phosphide, zinc sulfide, zinc selenide, cadmium mercury telluride, and cadmium selenide sulfide. Other suitable quantum dots may be based upon semiconducting polymers or organic molecules, such as dyes. The quantum dots may substantially comprise a single semiconductor material, or they may be core-shell quantum dots comprising multiple semiconductor materials. Homogenously mixed semiconductor materials within quantum dots may be used similarly. In some embodiments, the quantum dots may be functionalized, such as with carboxylic acid groups, to modify their spectral properties. Surface functionalization may alter the band gap and change the wavelengths of electromagnetic radiation with which the quantum dots most effectively optically interact.

In some embodiments, the quantum dots may be immobilized in a polymer when disposed within the quantum dot array. In some other embodiments, a surface coating may be applied over the integrated computational element to maintain the quantum dots in position. Suitable polymers and coating materials are not believed to be particularly limited.

Characteristics of a sample that may be analyzed according to the present disclosure are not believed to be particularly limited. Illustrative characteristics that may be assayed using an integrated computational element of the present disclosure to mimic a regression vector associated therewith include, for example, analyte concentrations, impurity content, viscosity, density, opacity, color, refractive index, liquid content, oxidation state, particle size, pH, salinity, total dissolved solids, ionic strength, porosity, bacteria content, combinations thereof, and the like. As mentioned above, various subsets of quantum dots within the quantum dot array may be used to analyze for a multiple characteristics of a sample.

Accordingly, methods for determining a characteristic of a sample are also contemplated using the integrated computational elements of the present disclosure. In various embodiments, such methods may comprise: providing an integrated computational element comprising a quantum dot array having a plurality of quantum dots disposed at a plurality of set array positions; optically interacting electromagnetic radiation with a sample and the integrated computational element; wherein the quantum dots located at one or more of the set array positions have spectral features such that optical interaction of the electromagnetic radiation with the quantum dots at the one or more set array positions substantially mimics a regression vector for at least one characteristic of the sample; receiving at a detector the electromagnetic radiation that has optically interacted with the sample and the integrated computational element; and determining the at least one characteristic of the sample based upon an output from the detector. Determination of the at least one characteristic may involve calculating the dot product of the regression vector in situ with the integrated computational element as discussed in more detail above.

Since both array and non-array detectors may receive electromagnetic radiation from quantum dots that are not used to substantially mimic the regression vector, methods of the present disclosure may further comprise disregarding electromagnetic radiation received at the detector from any set array positions containing quantum dots that are not used to substantially mimic the regression vector upon their optical interaction with the electromagnetic radiation. Illustrative ways in which the electromagnetic radiation may be disregarded are discussed in more detail above. Further, the methods of the present disclosure may further comprise computationally combining a plurality of signals from the detector corresponding to electromagnetic radiation received from quantum dots at each of the one or more set array positions used to substantially mimic the regression vector.

In some embodiments, methods of the present disclosure may comprise exposing all of the quantum dots in the quantum dot array to electromagnetic radiation at the same time. The electromagnetic radiation can be subsequently conveyed to a detector, and any electromagnetic radiation not used in substantially mimicking the regression vector may be disregarded.

In other embodiments, methods of the present disclosure may comprise rotating the integrated computational element, and exposing the quantum dots in only one of the set array positions to the electromagnetic radiation at a time. Again, any electromagnetic radiation received at the detector from any set array positions containing quantum dots that are not used to substantially mimic the regression vector may be disregarded.

In other various embodiments, methods of the present disclosure may further comprise: determining a first characteristic of the sample from electromagnetic radiation that has optically interacted with quantum dots in a first plurality of the set array positions, and determining a second characteristic of the sample from electromagnetic radiation that optically interacted with quantum dots in a second plurality of the set array positions. Again, the first characteristic and the second characteristic may differ from one another, and the first plurality of the set array positions and the second plurality of the set array positions may also differ from one another.

Given the description above, it is to be recognized that the optical analysis tools of the present disclosure may be used for determining characteristics of various samples, particularly fluids. In some embodiments, the methods may comprise flowing a fluid between a source of electromagnetic radiation and a detector. The integrated computational element containing a quantum dot array may be disposed along an optical pathway before or after the electromagnetic radiation optically interacts with the sample. In alternative embodiments, the sample may be static when undergoing analysis.

In more specific embodiments, the sample may comprise a treatment fluid or a formation fluid. Illustrative treatment fluids and treatment operations which may be analyzed according to the disclosure herein are specified hereinabove. Illustrative formation fluids that may be analyzed using the optical analysis tools of the present disclosure may include, for example, oil, formation water, natural gas, hydrogen sulfide, asphaltenes, and the like. In performing these analyses, the integrated computational element may be positioned on or near the earth's surface (e.g., in a pipeline), or in other embodiments, the integrated computational element may be positioned in a subterranean wellbore. Disposition of the integrated computational element in either location can allow proactive control and/or monitoring of a treatment operation to take place.

In some embodiments, the data collected using the optical analysis tools can be archived along with data associated with operational parameters being logged at a job site. Evaluation of job performance can then be assessed and improved for future operations or such information can be used to design subsequent operations. In addition, the data and information can be communicated (wired or wirelessly) to a remote location by a communication system (e.g., satellite communication or wide area network communication) for further analysis. The communication system can also allow remote monitoring and operation of a process to take place. Automated control with a long-range communication system can further facilitate the performance of remote job operations. In particular, an artificial neural network can be used in some embodiments to facilitate the performance of remote job operations. That is, remote job operations can be conducted automatically in some embodiments. In other embodiments, however, remote job operations can occur under direct operator control, where the operator is not at the job site.

Embodiments Herein Include:

A. Optical analysis tools. The optical analysis tools comprise: an electromagnetic radiation source that provides electromagnetic radiation to an optical pathway; an integrated computational element positioned at least partially within the optical pathway, the integrated computational element comprising a quantum dot array having a plurality of quantum dots disposed at a plurality of set array positions; wherein the quantum dots located at one or more of the set array positions have spectral features such that optical interaction of the electromagnetic radiation with the quantum dots at the one or more set array positions substantially mimics a regression vector for at least one characteristic of a sample that also optically interacts with the electromagnetic radiation; and a detector that receives the electromagnetic radiation from the optical pathway after the electromagnetic radiation has optically interacted with the sample and the integrated computational element.

B. Methods for determining a characteristic using an integrated computational element containing a quantum dot array. The methods comprise: providing an integrated computational element comprising a quantum dot array having a plurality of quantum dots disposed at a plurality of set array positions; optically interacting electromagnetic radiation with a sample and the integrated computational element; wherein the quantum dots located at one or more of the set array positions have spectral features such that optical interaction of the electromagnetic radiation with the quantum dots at the one or more set array positions substantially mimics a regression vector for at least one characteristic of the sample; receiving at a detector the electromagnetic radiation that has optically interacted with the sample and the integrated computational element; and determining the at least one characteristic of the sample based upon an output from the detector.

Each of embodiments A and B may have one or more of the following additional elements in any combination:

Element 1: wherein optical interaction of the electromagnetic radiation with the quantum dots from less than all of the set array positions substantially mimics the regression vector for the at least one characteristic of the sample.

Element 2: wherein the optical analysis tool is configured to disregard electromagnetic radiation received at the detector from any set array positions containing quantum dots that are not used to substantially mimic the regression vector upon optical interaction with the electromagnetic radiation.

Element 3: wherein the detector comprises an array detector that receives the electromagnetic radiation simultaneously from each of the set array positions.

Element 4: wherein the array detector comprises a blank detection region that is not exposed to electromagnetic radiation.

Element 5: wherein the optical analysis tool is configured to computationally combine a plurality of signals from the detector corresponding to electromagnetic radiation received from quantum dots at each of the one or more set array positions used to mimic the regression vector.

Element 6: wherein optical interaction of the electromagnetic radiation with the quantum dots in a first plurality of the set array positions substantially mimics a regression vector for a first characteristic of the sample, and optical interaction of the electromagnetic radiation with the quantum dots in a second plurality of the set array positions substantially mimics a regression vector for a second characteristic of the sample, the first characteristic and the second characteristic differing from one another, and the first plurality of set array positions and the second plurality of set array positions differing from one another.

Element 7: wherein the quantum dot array contains at least one set array position that lacks quantum dots.

Element 8: wherein each set array position in the quantum dot array contains quantum dots having spectral properties differing from those in other set array positions.

Element 9: wherein the integrated computational element is rotatable.

Element 10: wherein the optical analysis tool exposes only one set array position to the electromagnetic radiation at a time as the integrated computational element is rotated.

Element 11: wherein the method further comprises: disregarding electromagnetic radiation received at the detector from any set array positions containing quantum dots that are not used to substantially mimic the regression vector upon optical interaction with the electromagnetic radiation.

Element 12: wherein the method further comprises: computationally combining a plurality of signals from the detector corresponding to electromagnetic radiation received from quantum dots at each of the one or more set array positions used to mimic the regression vector.

Element 13: wherein the method further comprises: determining a first characteristic of the sample from electromagnetic radiation that has optically interacted with quantum dots in a first plurality of the set array positions; and determining a second characteristic of the sample from electromagnetic radiation that has optically interacted with quantum dots in a second plurality of the set array positions; wherein the first characteristic and the second characteristic differ from one another, and the first plurality of set array positions and the second plurality of set array positions differ from one another.

Element 14: wherein the method further comprises: rotating the integrated computational element; and exposing the quantum dots in only one of the set array positions to the electromagnetic radiation at a time.

Element 15: wherein the sample comprises a treatment fluid or a formation fluid.

Element 16: wherein the integrated computational element is positioned in a subterranean wellbore.

By way of non-limiting example, exemplary combinations applicable to A and B include:

The optical analysis tool of A in combination with elements 1 and 2; 1 and 3; 3 and 4; 1 and 5; 1 and 6; 4 and 7; 2 and 8; 2, 3 and 8; 9 and 10; 2, 9 and 10; 5, 9 and 10; and 2, 5, 9 and 10.

The method of B in combination with elements 1 and 3; 3 and 4; 4 and 7; 2 and 8; 2, 3 and 8; 9 and 10; 3 and 11; 1, 3 and 11; 3, 11 and 12; 1,3, 11 and 12; 1 and 13; 3 and 13; 11 and 14; 12 and 14; 11, 12 and 14; 1, 3 and 15; 3 and 15; and 15 and 16.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The disclosure illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. An optical analysis tool comprising:
   an electromagnetic radiation source that provides electromagnetic radiation to an optical pathway;
   an integrated computational element positioned at least partially within the optical pathway, the integrated computational element comprising a quantum dot array having a plurality of quantum dots disposed at a plurality of set array positions;
      wherein the quantum dots located at one or more of the set array positions have spectral features such that optical interaction of the electromagnetic radiation with the quantum dots at the one or more set array positions substantially mimics a regression vector for at least one characteristic of a sample that also optically interacts with the electromagnetic radiation; and
   a detector that receives the electromagnetic radiation from the optical pathway after the electromagnetic radiation has optically interacted with the sample and the integrated computational element.

2. The optical analysis tool of claim 1, wherein optical interaction of the electromagnetic radiation with the quantum dots from less than all of the set array positions substantially mimics the regression vector for the at least one characteristic of the sample.

3. The optical analysis tool of claim 2, wherein the optical analysis tool is configured to disregard electromagnetic radiation received at the detector from any set array positions containing quantum dots that are not used to substantially mimic the regression vector upon optical interaction with the electromagnetic radiation.

4. The optical analysis tool of claim 3, wherein the detector comprises an array detector that receives the electromagnetic radiation simultaneously from each of the set array positions.

5. The optical analysis tool of claim 4, wherein the array detector comprises a blank detection region that is not exposed to electromagnetic radiation.

6. The optical analysis tool of claim 3, wherein the optical analysis tool is configured to computationally combine a plurality of signals from the detector corresponding to electromagnetic radiation received from quantum dots at each of the one or more set array positions used to mimic the regression vector.

7. The optical analysis tool of claim 1, wherein optical interaction of the electromagnetic radiation with the quantum dots in a first plurality of the set array positions substantially mimics a regression vector for a first characteristic of the sample, and optical interaction of the electromagnetic radiation with the quantum dots in a second plurality of the set array positions substantially mimics a regression vector for a second characteristic of the sample, the first characteristic and the second characteristic differing from one another, and the first plurality of set array positions and the second plurality of set array positions differing from one another.

8. The optical analysis tool of claim 1, wherein the quantum dot array contains at least one set array position that lacks quantum dots.

9. The optical analysis tool of claim 1, wherein each set array position in the quantum dot array contains quantum dots having spectral properties differing from those in other set array positions.

10. The optical analysis tool of claim 1, wherein the integrated computational element is rotatable.

11. The optical analysis tool of claim 10, wherein the optical analysis tool exposes only one set array position to the electromagnetic radiation at a time as the integrated computational element is rotated.

12. The optical analysis tool of claim 11, wherein the optical analysis tool is configured to disregard electromagnetic radiation received at the detector from any set array positions containing quantum dots that are not used to substantially mimic the regression vector upon optical interaction with the electromagnetic radiation.

13. The optical analysis tool of claim 12, wherein the optical analysis tool is configured to computationally combine a plurality of signals from the detector corresponding to electromagnetic radiation received from quantum dots at each of the one or more set array positions used to mimic the regression vector.

14. A method comprising:
   providing an integrated computational element comprising a quantum dot array having a plurality of quantum dots disposed at a plurality of set array positions;
   optically interacting electromagnetic radiation with a sample and the integrated computational element;
      wherein the quantum dots located at one or more of the set array positions have spectral features such that optical interaction of the electromagnetic radiation with the quantum dots at the one or more set array positions substantially mimics a regression vector for at least one characteristic of the sample;
   receiving at a detector the electromagnetic radiation that has optically interacted with the sample and the integrated computational element; and
   determining the at least one characteristic of the sample based upon an output from the detector.

15. The method of claim 14, wherein optical interaction of the electromagnetic radiation with the quantum dots from less than all of the set array positions substantially mimics the regression vector for the at least one characteristic of the sample.

16. The method of claim 15, wherein the detector comprises an array detector that receives the electromagnetic radiation simultaneously from each of the set array positions.

17. The method of claim 16, further comprising:
disregarding electromagnetic radiation received at the detector from any set array positions containing quantum dots that are not used to substantially mimic the regression vector upon optical interaction with the electromagnetic radiation.

18. The method of claim 17, further comprising:
computationally combining a plurality of signals from the detector corresponding to electromagnetic radiation received from quantum dots at each of the one or more set array positions used to substantially mimic the regression vector.

19. The method of claim 14, further comprising:
determining a first characteristic of the sample from electromagnetic radiation that has optically interacted with quantum dots in a first plurality of the set array positions; and
determining a second characteristic of the sample from electromagnetic radiation that has optically interacted with quantum dots in a second plurality of the set array positions;
wherein the first characteristic and the second characteristic differ from one another, and the first plurality of set array positions and the second plurality of set array positions differ from one another.

20. The method of claim 14, further comprising:
rotating the integrated computational element; and
exposing the quantum dots in only one of the set array positions to the electromagnetic radiation at a time.

21. The method of claim 20, further comprising:
disregarding electromagnetic radiation received at the detector from any set array positions containing quantum dots that are not used to substantially mimic the regression vector upon optical interaction with the electromagnetic radiation.

22. The method of claim 21, further comprising:
computationally combining a plurality of signals from the detector corresponding to electromagnetic radiation received from quantum dots at each of the one or more set array positions used to substantially mimic the regression vector.

23. The method of claim 14, wherein the sample comprises a treatment fluid or a formation fluid.

24. The method of claim 23, wherein the integrated computational element is positioned in a subterranean wellbore.

* * * * *